United States Patent [19]

Rubenstein et al.

[11] Patent Number: 5,417,225
[45] Date of Patent: May 23, 1995

[54] SURGICAL RADIATION SHIELD HAVING AN OPENING FOR TUBE INSERTION AND A SLIT FOR SHIELD REMOVAL WITHOUT TUBE REMOVAL

[75] Inventors: Jon R. Rubenstein, Augusta, W. Va.; John J. Pahira, McLean; Alan G. Taylor, Falls Church, both of Va.

[73] Assignee: Georgetown University, Washington, D.C.

[21] Appl. No.: 116,273

[22] Filed: Sep. 3, 1993

[51] Int. Cl.$^6$ .................................................. A61B 6/10
[52] U.S. Cl. .................................... 128/849; 128/853; 250/516.1; 250/519.1; 428/71; 428/74
[58] Field of Search .......................... 128/849–857; 250/515.1–519.1; 428/71, 74, 318.4, 319.3

[56] References Cited

U.S. PATENT DOCUMENTS

| | | |
|---|---|---|
| 2,794,128 | 5/1957 | Shasky . |
| 2,858,410 | 10/1958 | Rich ..................................... 219/539 |
| 3,030,957 | 4/1962 | Milges ................................... 128/853 |
| 3,292,179 | 12/1966 | Iacono, Jr. et al. ........................ 2/2 |
| 3,394,260 | 7/1968 | Phipps ................................ 250/516.1 |
| 3,799,161 | 3/1974 | Collins . |
| 3,926,185 | 12/1975 | Kizewinski ........................... 128/854 |
| 3,930,497 | 1/1976 | Krebs et al. . |
| 3,942,023 | 3/1976 | Flaugnatti . |
| 3,944,838 | 3/1976 | Gäde . |
| 4,041,942 | 8/1977 | Dougan et al. . |
| 4,214,167 | 7/1980 | Gäde . |
| 4,479,492 | 10/1984 | Singer ................................... 128/853 |
| 4,581,538 | 4/1986 | Lenhart . |
| 4,670,658 | 6/1987 | Meyers ............................... 250/519.1 |
| 4,876,135 | 10/1989 | McIntosh ............................... 428/74 |
| 4,910,803 | 3/1990 | Cukier . |
| 4,938,233 | 7/1990 | Orrison, Jr. . |
| 4,941,882 | 7/1990 | Ward et al. ..................... 128/DIG. 26 |
| 4,945,924 | 8/1990 | Poettgen .............................. 128/849 |
| 5,006,718 | 4/1991 | Lenhart . |
| 5,012,114 | 4/1991 | Sisson, Jr. . |
| 5,028,468 | 7/1991 | Taylor .................................... 428/71 |
| 5,038,047 | 8/1991 | Still ...................................... 128/857 |
| 5,109,873 | 5/1992 | Marshall ............................... 128/849 |
| 5,151,314 | 9/1992 | Brown . |

FOREIGN PATENT DOCUMENTS 1164093 10/1958 France .
2614202 10/1977 Germany .

OTHER PUBLICATIONS

Operating Room Technic, 4th ed., W. B. Saunders Co., 1952, pp. 295–311.

Primary Examiner—Robert A. Hafer
Assistant Examiner—Michael O'Neill
Attorney, Agent, or Firm—Oliff & Berridge

[57] ABSTRACT

A radiation shield includes an aperture connected to an edge of the shield by a slit, which is held closed by a releasable flap. Instrumentation can be inserted through the aperture to contact a patient over which the shield is draped. By releasing the flap and thereby opening the aperture toward the edge of the shield, the shield can be removed from the patient without removing the instrumentation inserted through the aperture. A secondary shield is releasably secured over the aperture, affording further protection. Because the shield is placed within the septic field during use, the shield includes a sterilizable outer covering.

24 Claims, 3 Drawing Sheets

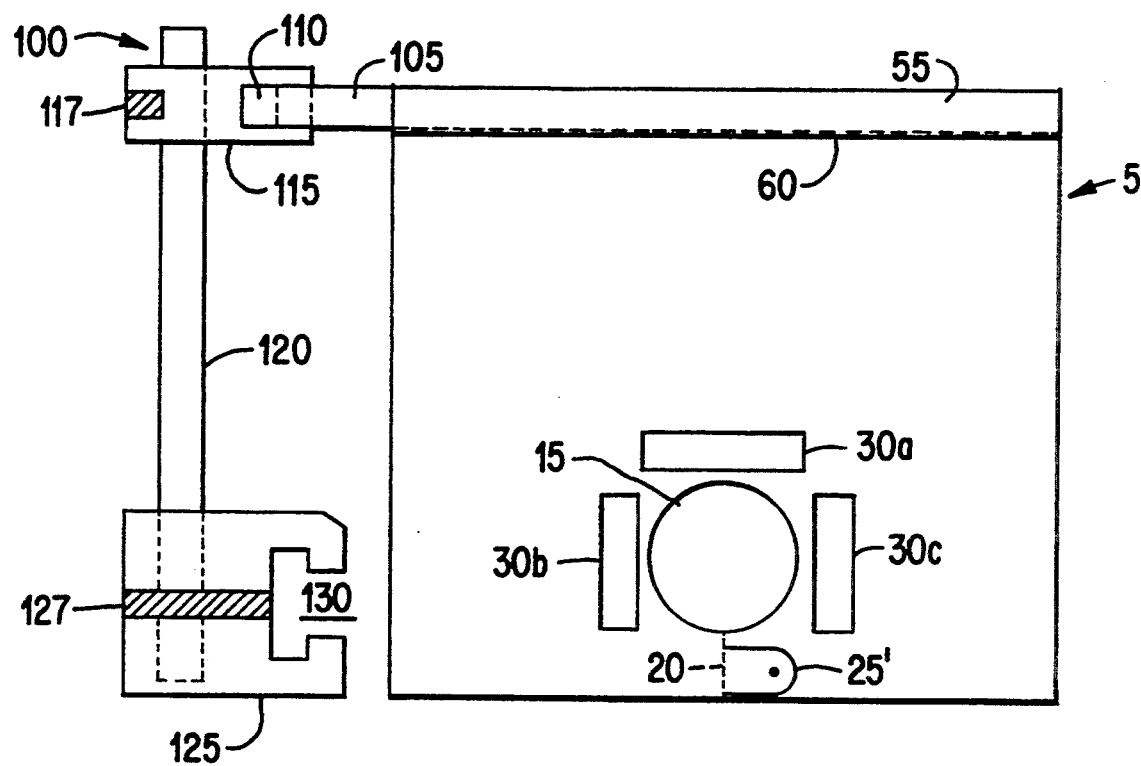
FIG. 4
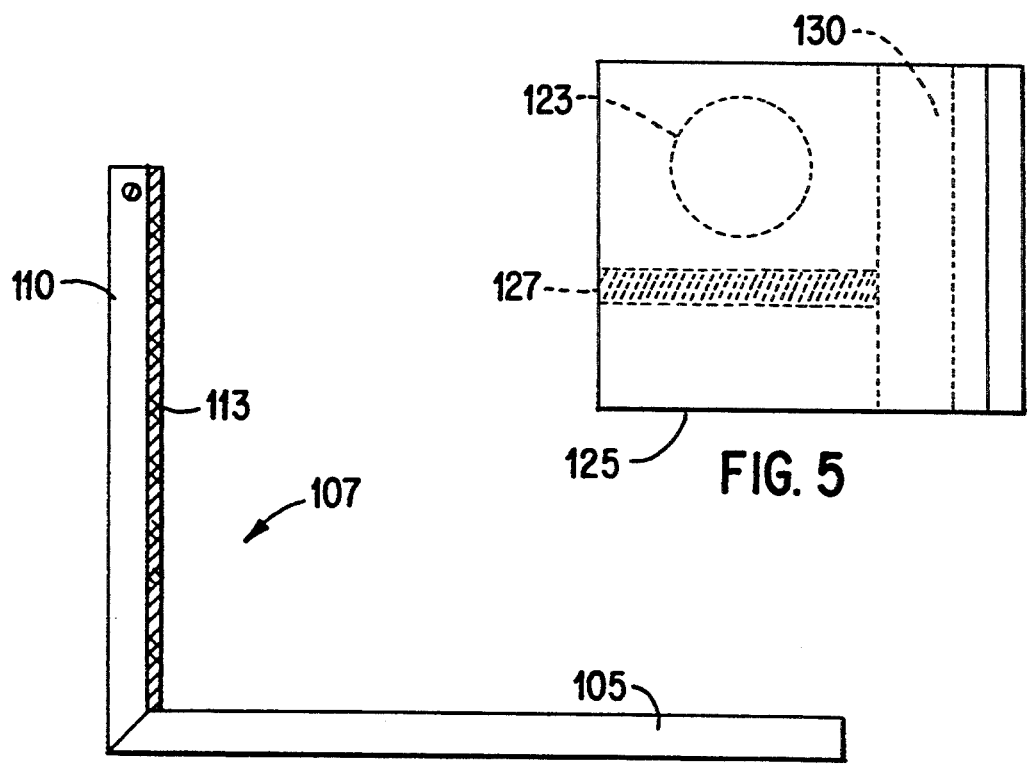
FIG. 5
FIG. 6

SURGICAL RADIATION SHIELD HAVING AN OPENING FOR TUBE INSERTION AND A SLIT FOR SHIELD REMOVAL WITHOUT TUBE REMOVAL

BACKGROUND OF THE INVENTION

1. Field of the Invention

The invention relates to radiation shields, and more particularly to surgical radiation shields having an aperture allowing removal of the shield without removal of surgical instruments inserted through the aperture.

2. Related Art

Electromagnetic radiation is used extensively in various invasive surgical procedures, such as fluoroscopic guidance and manipulation of surgical instruments. To protect operating room personnel from scattered radiation, shielding is commonly employed. Currently available surgical radiation :shields are designed primarily to attenuate radiation either above or below the patient plane. Such shields provide limited protection for operating room personnel from a significant radiation source—the patient upon whom the surgical procedure is being performed.

Modern fluoroscopic equipment, used in many surgical procedures, provides fine primary beam collimation and very minimal X-ray tube radiation leakage. But when X-ray radiation interacts with a patient, significant radiation is scattered through and from the patient. This scattered radiation is the leading source of exposure to attending personnel. Exposure rates in excess of one rem/hour have been measured.

U.S. Pat. No. 4,581,538 to Lenhart exemplifies the inadequacies of the prior art. As shown in FIGS. 1 and 4 of Lenhart, curtain 40 of shield 16 is positioned above the patient plane, allowing X-rays from X-ray source 14 to scatter through and from the patient to attending personnel 20, 22, 24. The Lenhart shield permits significant radiation exposure.

U.S. Pat. No. 4,938,233 to Orrison, Jr. exemplifies another disadvantage of the prior art. In an emergency, such as cardiac arrest, surgical radiation shielding must be removed from the patient as quickly as possible. In Orrison, although protective drape 130 extends both above and below the patient plane, as shown, for example, in FIG. 13A, drape 130 is not readily removable from the patient in an emergency. Catheter instrumentation is inserted through cut-out 132, necessitating removal of such instrumentation before removal of drape 130. Removing the instrumentation wastes precious time, increasing the danger to the patient. A further disadvantage of the Orrison drape is that X-rays must be precisely directed through narrow drape opening 134. If the beam is even slightly misaligned with opening 134, the beam will contact the drape and be scattered therefrom. Moreover, diagnostic-quality images could not even be obtained when using the Orrison drape. Biplanar imaging, that is, imaging on two or more planes or from two or more angles, is impossible with the Orrison drape, because X-rays can be directed only through drape opening 134.

Vertical, plate-like radiation shields, positioned between the X-ray source and operating room personnel, have also been used. In certain procedures, such as urologic procedures, such vertical shields provide inadequate protection, because the surgeon's head is often positioned below the plane of the bottom of the shield, which is above the plane of the patient. The shield, therefore, allows electromagnetic radiation scattered from the patient to contact the surgeon.

There is, accordingly, a need for a radiation shield that adequately protects attending personnel from scattered radiation and also allows quick removal of the shield from a patient in an emergency.

SUMMARY OF THE INVENTION

It is an object of the invention to provide a surgical radiation shield capable of better protecting operating room personnel than is currently available.

It is a further object of the invention to provide a surgical radiation shield that is easily removable from the patient, without removing surgical instrumentation from the patient, in an emergency.

To achieve this and other objects, the shield according to the invention includes an electromagnetic-radiation-attenuating layer with an aperture disposed therein and an opening extending from the aperture toward the layer periphery. The aperture allows instrumentation to be inserted though. the aperture, and the opening allows the shield to be moved without moving the instrumentation.

In a preferred embodiment, a closure element, such as a flap, releasably holds the opening in a closed position, better securing the shield and affording maximum protection to attending personnel. The flap is itself preferably formed. of an electromagnetic-radiation-attenuating material.

According to another aspect of the invention, a secondary layer of electromagnetic-radiation-attenuating material is provided, releasably secured in place over the aperture. The secondary layer is preferably divided into two leaves, allowing the layer to cover the aperture while instrumentation remains inserted through the aperture, affording maximum protection to attending personnel. The secondary shield is preferably secured over the aperture by VELCRO or other suitable fastening devices.

According to still another aspect of the invention, the shield includes a means for supporting the shield in a hanging position above the patient so as to contact the patient. In a preferred embodiment, the supporting means comprises a loop extending across an upper region of the shield.

According to still another aspect of the invention, a sterilizable cover may be provided to surround the layer. The cover preferably includes at least one inside seam or a hermetically sealed seam. A disposable, sterilizable bag that surrounds the layer can be also provided.

According to still another aspect of the invention, there is provided a support frame having a support member from which the shield hangs, a post supporting the support member, and an attachment member that supports the post and is attachable to an accessory rail of an operating table. The support member is preferably rotatable in a horizontal plane on the post to swing the shield from a position substantially perpendicular to the patient to a position substantially parallel to the patient.

Finally, according to another aspect of the invention, there is provided a shield having a layer of electromagnetic-radiation-attenuating material, an at least semi-transparent covering on the outside of at least part of the layer, and moisture-indicating material disposed between the covering and the layer, wherein the moisture-indicating material provides an indication, visible through the covering, if moisture passes the covering.

These and other features of the invention are described in or apparent from the detailed description of preferred embodiments.

BRIEF DESCRIPTION OF THE DRAWINGS

The preferred embodiments are described with reference to the drawings, in which like reference numerals denote like elements throughout the Figures, and in which:

FIG. 4 is a front view of a shield supported by a stand, according to the invention;

FIG. 5 is a top plan view of an attachment clamp according to the invention;

FIG. 6 is a top plan view of an L-shaped support member according to the invention;

DETAILED DESCRIPTION OF PREFERRED EMBODIMENTS

Figure 1:
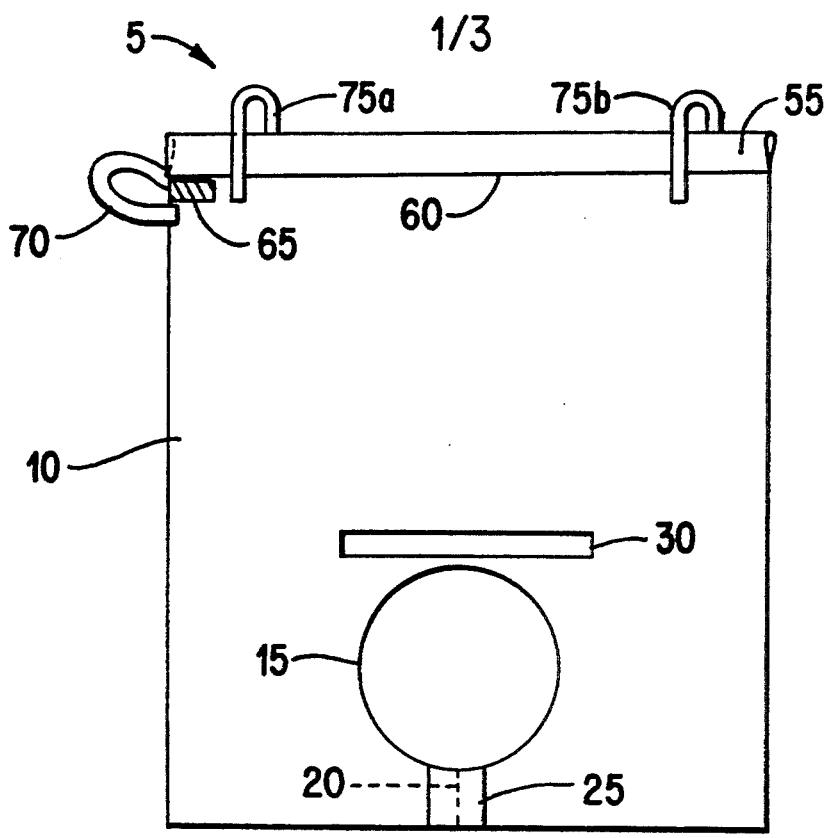
FIG. 1 is a front view of a surgical radiation shield according to the invention.

As shown in FIG. 1, radiation shield 5 includes layer 10 of electromagnetic-radiation-attenuating material, preferably having at least a 0.5 mm lead equivalent shielding value. Layer 10 is preferably formed of one of the currently available ultralight shielding materials.

Aperture 15 extends through layer 10 and is connected to the edge of the layer by a slit-like opening 20. A closure element such as flap 25 extends from one side of opening 20 to the other side, to hold opening 20 closed. At least one end of flap 25 includes means for releasably securing the flap in place, such as VELCRO, adhesive tape, clasps, etc. Flap 25 thus holds together the two sides of layer 10 below aperture 15, but is releasable to uncover and open aperture 15 to the periphery of layer 10. To prevent radiation form passing through opening 20, flap 25 is formed of radiation-attenuating material similar to that of layer 10. FIG. 4 shows an alternate, curved flap 25', similar in structure, function and securement as flap 25 of FIG. 1.

Figure 2:
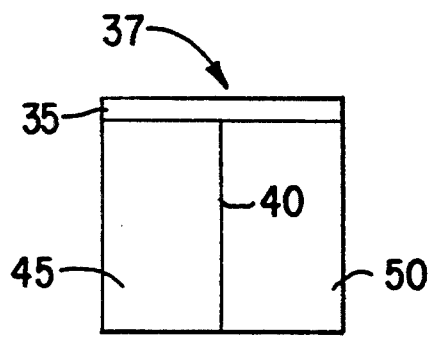
FIG. 2 is a front view of a secondary shield according to the invention.

A strip 30 of VELCRO, or a similarly functioning material, extends above aperture 15 and releasably holds secondary shield 37, illustrated in FIG. 2, in place over aperture 15. Secondary shield 37 is formed of a secondary radiation-attenuating material layer similar to layer 10 and includes two leaves 45, 50, divided by cut 40. Strip 35, formed of material similar to strip 30, extends across secondary shield 37. Alternately, as shown in FIG. 4, three strips 30a-c of VELCRO or similar material can be provided to better secure secondary shield 37, which can be provided with three corresponding strips, over aperture 15.

Strips 30 or 30a-c can be disposed on both sides of shield 5, allowing secondary shield 37 to be attached on either side, as desired. Shield 5, therefore, is reversible.

At the upper end of shield 5, layer 10 is folded into loop 55 secured by seam 60, enabling shield 5 to be supported in a hanging position during a surgical procedure, as described below. Nylon straps 75a,b extend around loop 55 so that shield. 5 can be stored in a hanging position between uses. Further, at least one nylon strap 70 with VELCRO or similar fastening strip 65 is provided on a side of shield 5, to prevent the shield from moving on its support frame during use.

Figure 3:
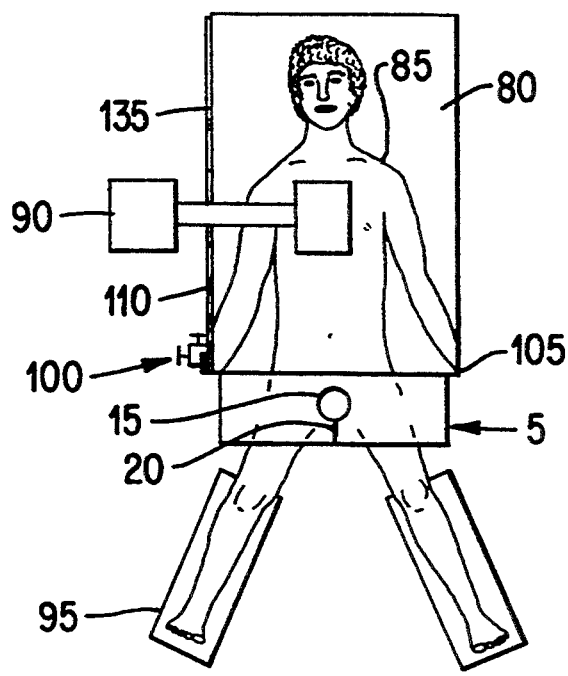
FIG. 3 is a top plan view showing a surgical radiation shield according to the present invention in use.

FIG. 3 shows a preferred use of shield 5 during a urologic procedure. Support frame 100, attached to accessory rail 135 of operating table 80, supports shield 5 in a hanging position,, so that the shield contacts patient 85 and aperture 15 is centered over the patient's genital area. The portions of shield 5 on opposite sides of aperture 15 drape over the patient's legs. Attending personnel, positioned, for example, between stirrups 95 supporting the patient's legs, insert surgical instrumentation, such as a catheter or cystoscope, through aperture 15 into patient 85. Shield 5 shields the personnel between stirrups 95 from contact with X-rays originating from X-ray source 90 and emanating from patient 85. Secondary shield 37 may be secured over aperture 15, the instruments extending through cut 40, to provide further protection.

Figure 7:
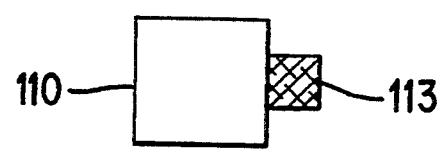
FIG. 7 is a cross-sectional view of an extension of the support member according to the invention.

As shown in FIGS. 4 and 6, support frame 100 includes L-shaped support member 107 having rod 105 extending through loop 55 in the shield and having extension 110. Extension 110 includes keyway 113, shown in FIGS. 6 and 7, and is slidably held within mounting bracket 115 to allow linear adjustment. Keyway 113 prevents downward tilting of support member 107 due to the weight of shield 5. Post 120 rotatably supports mounting bracket 115, allowing support member 107 and shield 5 to swing from a position substantially perpendicular to the patient, as shown in FIG. 3, to a position substantially parallel to the patient. Loop 70 on shield 5 can loop around post 120 to prevent shield 5 from sliding off rod 105. Bracket 115 is also slidable along post 120 for vertical adjustment. Attachment clamp 125 defines a C-shaped opening 130 for receiving and sliding along accessory rail 135 of operating table 80 and also has an opening 123, shown in FIG. 5, for receiving post 120. Threaded openings 117, 127 receive clamping elements (not shown) to tighten bracket 115 and clamp 125 to post 120.

During a surgical emergency in which shield 5 must be quickly removed from patient 85, operating room personnel can remove the shield without dislodging the surgical instruments inserted into the patient through aperture 15. One end of flap 25 is released, opening aperture 15 to the periphery of the shield by slit-like opening 20. Rod 105 of support frame 100 is then swung in a horizontal plane on support post 120 to remove shield 5 from the vicinity of patient 85. Alternate removal methods, such as disengaging clamp 125 from accessory rail 135, may also be employed after flap 25 has been released.

In an alternate embodiment, shield 5 can be attached to a floor stand equipped with casters, allowing greater mobility. Such a floor stand, however, has at least two disadvantages: the relative positioning of the shield and patient will change as the operating table is moved, and many fluoroscopic tables have fragile, bottom-mounted cameras, easily damageable upon collision with a floor stand. Additionally, floor stands contribute to surgical suite crowding and pose a tripping hazard.

In another alternate embodiment, the shield can be hung from the ceiling on a retractable arm. A ceiling-hung shield eliminates the tripping and crowding problem, but the shield still does not maintain the same relative position to the patient during movement of the operating table.

Figure 8:
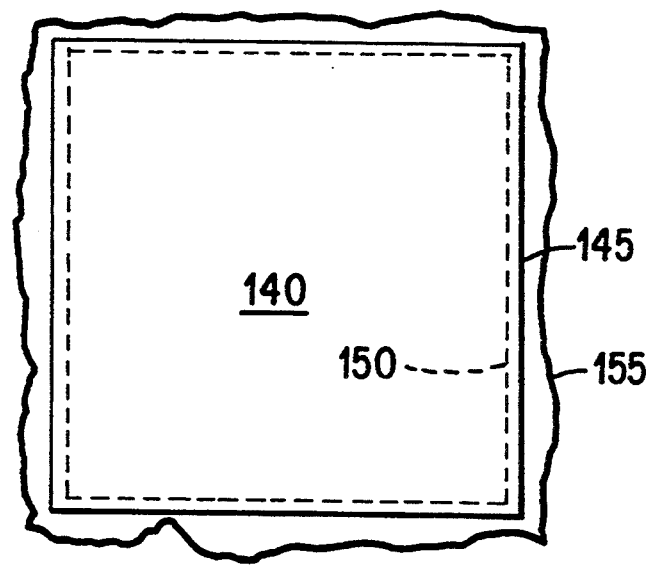
FIG. 8 is a front view showing shield coverings according to the invention.

Because shield 5 is placed within the septic field during surgical procedures, effectively sterilizing the shield is key. As shown in FIG. 8, therefore, shield 5 (as well as secondary shield 37) has an outer covering 140 that surrounds layer 10. In one embodiment, outer covering 140 is designed with inside seams 150, similar to the seams on the inside of a pillowcase, for example. After use, infectious material can be wiped away from the shield using an antiseptic solution, followed by gas autoclave sterilization. Multiple patients can be accommodated by using multiple shields.

In an alternate embodiment, outer covering 140 includes hermetically sealed seams, eliminating the need for autoclave sterilization. The shield can be adequately cleaned by applying an antiseptic cleanser and immersing the shield in a cleaning solution. In a preferred embodiment, outer covering 140 is constructed of silicon rubber sheeting, and the hermetically sealed seams are produced by heat sealing and/or adhesive. Heat sealing yields a very durable, moisture-free seal.

Sheets of silicon rubber are semi-transparent. A sheet of commercially available moisture-indicating material 145 can be placed inside the silicon covering and located in a readily visible position. In this arrangement, any moisture penetrating the covering is immediately recognizable. If moisture penetrates the covering during sterilization soaking, the inside layer of the shield should be allowed to dry prior to use.

Alternatively, hermetic seams can be produced in an outer covering 140 formed of polyvinyl chloride sheets, the current industry standard for personnel-shielding apparel. Although this material can be heat sealed, it is subject to embrittlement, which reduces durability. An alternate seam can be produced by pressure-gluing the sheets together using a commercially available, preferably acrylic-based adhesive.

In conjunction with either the inside seam or hermetically-sealed seam embodiments, disposable bag 155, preferably formed of plastic and conforming to the shape of the shield, can be placed around outer covering 140 and discarded after use. Bag 155 can also be used without outer covering 140, directly covering layer 10.

Although a variety of dimensions are possible, in a particular embodiment shield 5 is 70 cm wide and 90 cm high, the aperture is 15 cm in diameter and spaced 25 cm from the nearest shield edge, and secondary layer 37 is preferably 25 cm by 20 cm. An advantage of sizing the shield in this general way is that the shield can extend between the patient and the X-ray source, thereby eliminating a separate shield surrounding the X-ray source.

While the invention has been described in conjunction with specific embodiments thereof, it is evident that many alternatives, modifications and variations will be apparent to those skilled in the art. For example, non-surgical uses of the shield are contemplated, and a variety of support arrangements may be employed to hold the shield in a desired position. Further, while the shield has been described for use in urologic procedures, aperture 15 and slit 20 can be strategically placed in the shield to accommodate any surgical procedure. Accordingly, the preferred embodiments of the invention as set forth herein are intended to be illustrative, not limiting. Various other changes may be made without departing from the spirit and scope of the invention.

What is claimed is:

1. A radiation shield for attenuating electromagnetic radiation, comprising:

an electromagnetic-radiation-attenuating drape formed of lead-equivalent material;

an aperture through the drape and spaced from edges of the drape, allowing insertion of surgical equipment through the aperture to a patient;

a slit extending from the aperture to one of the edges of the drape;

a flap extending at least partially over the slit to hold the slit closed; and a secondary shield formed of lead-equivalent electromagnetic-radiation-attenuating material, the secondary shield being releasably secured to the drape to cover the aperture.

2. The shield of claim 1, wherein the flap is formed of lead equivalent electromagnetic-radiation-attenuating material.

3. The shield of claim 1, further comprising means for releasably securing at least one end of the flap to the drape on one side of the slit to hold the slit closed, wherein the securing means allows the one flap end to be disengaged from the drape, thereby opening the aperture to said one drape edge and permitting the drape to be removed from the vicinity of the patient without removing the equipment inserted through the aperture.

4. The shield of claim 1, wherein the secondary shield is releasably secured to the drape so as to be completely removable from the drape.

5. The shield of claim 1, further comprising:

a covering formed of sterilizable, surgical material, the covering being disposed on the outside of at least part of the drape and being at least semi-transparent; and moisture-indicating material disposed between the lead-equivalent material and the covering to provide an indication, visible through the covering, when moisture passes the covering.

6. A shield for attenuating electromagnetic radiation, comprising:

a primary layer of electromagnetic-radiation-attenuating material having a periphery;

an aperture through the layer and spaced from the periphery of the layer, allowing insertion of instrumentation through the aperture;

an opening extending from the aperture toward the periphery, allowing the aperture to be opened toward the periphery and the shield to be moved without moving the instrumentation inserted through the aperture;

a secondary layer of electromagnetic-radiation-attenuating material covering the aperture through the primary layer; and a slit extending at least partially across the secondary layer, dividing the secondary layer into at least two leaves.

7. The shield of claim 6, further comprising a closure element for holding the opening closed.

8. The shield of claim 7, wherein the closure element comprises a flap extending across the opening.

9. The shield of claim 8, wherein the flap is formed of an electromagnetic-radiation-attenuating material.

10. The shield of claim 8, further comprising means for releasably securing the flap across the opening.

11. The shield of claim 6, wherein the opening comprises a slit in the layer extending from the aperture to a peripheral edge of the layer.

12. The shield of claim 11, wherein at least part of the slit is perpendicular to the peripheral edge.

13. The shield of claim 6, further comprising means for releasably securing the secondary layer over the aperture through the primary layer.

14. The shield of claim 13, wherein the securing means is disposed on opposite sides of the primary layer so that the secondary layer can be releasably secured over the aperture on either of the opposite sides of the layer.

15. The shield of claim 6, further comprising means for supporting the shield in a hanging position above a patient so that the shield contacts the patient.

16. The shield of claim 15, wherein the supporting means comprises a loop extending across an upper region of the shield.

17. The shield of claim 6, further comprising a sterilizable covering surrounding the layer, the covering comprising at least one inside seam.

18. The shield of claim 6, further comprising a sterilizable covering surrounding the layer, the covering comprising at least one hermetically sealed seam.

19. The shield of claim 6, further comprising a disposable sterilized bag surrounding the layer, the bag being replaceable after use of the shield.

20. A radiation shielding arrangement, comprising:
A) a shield for attenuating electromagnetic radiation, comprising:
   1) a primary layer of electromagnetic-radiation-attenuating material having a periphery;
   2) an aperture through the layer and spaced from the periphery of the layer, allowing insertion of instrumentation through the aperture;
   3) an opening extending from the aperture toward the periphery, allowing the aperture to be opened toward the periphery and the shield to be moved without moving the instrumentation inserted through the aperture;
   a secondary layer of electromagnetic-radiation-attenuating material covering the aperture through the primary layer;
   a slit extending at least partially across the secondary layer, dividing the secondary layer into at least two leaves; and
B) a support frame, comprising:
   1) a support member from which the shield hangs;
   2) a post that supports the support member; and
   3) an attachment member that supports the post.

21. The invention of claim 20, wherein the attachment member is attachable to an accessory rail of an operating table.

22. The invention of claim 20, wherein the support member is rotatable in a horizontal plane on the post to swing the shield from a hanging position substantially perpendicular to and contacting a patient to a hanging position substantially parallel to and out of contact with the patient.

23. A shield for attenuating electromagnetic radiation, comprising:
a primary layer of electromagnetic-radiation-attenuating material having a periphery;
an aperture through the layer and spaced from the periphery of the layer, allowing insertion of instrumentation through the aperture;
a primary opening in the primary layer extending from the aperture toward the periphery, allowing the aperture to be opened toward the periphery;
a secondary layer of electromagnetic-radiation-attenuating material covering the aperture through the primary layer;
a release mechanism for releasably securing the secondary layer to the primary layer; and
a secondary opening extending through the secondary layer allowing insertion of the instrumentation through both the aperture and secondary opening, the secondary layer surrounding the instrumentation while the primary opening and the release mechanism allow the shield to be moved without moving the instrumentation inserted through the aperture and secondary opening.

24. The shield of claim 23, wherein the secondary opening is a slit, a first portion of the slit accommodating the instrumentation and a second portion of the slit extending from the first portion to an edge of the secondary layer.

* * * * *